(12) United States Patent
Rauh

(10) Patent No.: US 7,441,951 B2
(45) Date of Patent: Oct. 28, 2008

(54) DRAWER FOR X-RAY DETECTORS

(75) Inventor: Peter Rauh, Schnabelwaid (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/997,461

(22) Filed: Nov. 24, 2004

(65) Prior Publication Data

US 2005/0152503 A1    Jul. 14, 2005

Related U.S. Application Data

(60) Provisional application No. 60/525,776, filed on Nov. 28, 2003.

(30) Foreign Application Priority Data

Nov. 28, 2003  (DE)  ................................ 103 56 288

(51) Int. Cl.
G03B 42/04     (2006.01)
(52) U.S. Cl. .................................. 378/167; 312/249.11
(58) Field of Classification Search .............. 312/334.8, 312/334.47, 249.9, 249.11, 319.1, 249; 384/17–23, 384/53; 378/167, 181, 172–173, 189, 210
See application file for complete search history.

(56) References Cited

U.S. PATENT DOCUMENTS

| | | | | |
|---|---|---|---|---|
| 4,183,596 A | * | 1/1980 | Greene et al. | ................ 312/333 |
| 4,416,022 A | * | 11/1983 | Cutter | ......................... 378/206 |
| 5,419,639 A | * | 5/1995 | Hobbs et al. | ................... 384/18 |
| 5,733,026 A | * | 3/1998 | Munachen | ............. 312/334.12 |
| 5,871,265 A | | 2/1999 | Stewart et al. | |
| 6,022,143 A | | 2/2000 | Helmreich | |
| 6,749,276 B2 | * | 6/2004 | Judge et al. | ............ 312/334.47 |
| 6,764,149 B2 | | 7/2004 | Jurja | |

(Continued)

FOREIGN PATENT DOCUMENTS

AT    340 631 A    12/1977

(Continued)

*Primary Examiner*—Hoon Song
(74) *Attorney, Agent, or Firm*—Brinks, Hofer, Gilson & Lione

(57) ABSTRACT

A telescoping rail for an X-ray detector drawer, which rail has at least three rail elements movable relatively to one another, namely a basic rail element, an intermediate rail element that is displaceable relative to the basic rail element, and an end rail element that is displaceable relative to the intermediate rail element. At least one driver is disposed between the rail elements. the driver is pivotably supported about a shaft oriented transversely or in inclined fashion to the displacement direction of the end rail element, and as a function of the intermediate rail element having been displaced out of the basic position, the driver is pivotable about the shaft into a slaving position which displaces the intermediate rail element along in the direction of the basic position until the basic position is reached, as a function of a displacement of the end rail element. As a function of a displacement of the intermediate rail element, the driver is pivotable past the basic position, out of the slaving position into a fundamental position which does not displace the intermediate rail element along. Moreover, in the fundamental position, the driver can enter into mutual engagement with the basic rail element so as to firmly hold the intermediate rail element in the basic position.

16 Claims, 5 Drawing Sheets

U.S. PATENT DOCUMENTS

2002/0150214 A1  10/2002  Siemens

FOREIGN PATENT DOCUMENTS

| DE | 38 36 273 A | 4/1990 |
| DE | 39 30 713 A | 3/1991 |
| DE | 39 30 713 A1 | 3/1991 |
| DE | 3930713 * | 3/1991 |
| DE | 38 36 273 A1 | 1/1998 |
| PL | AT 340 631 | 4/1977 |

* cited by examiner

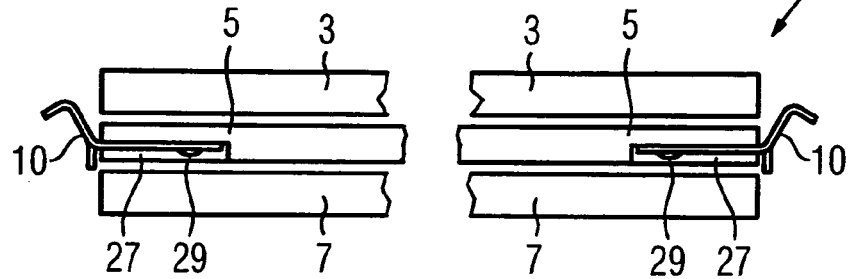
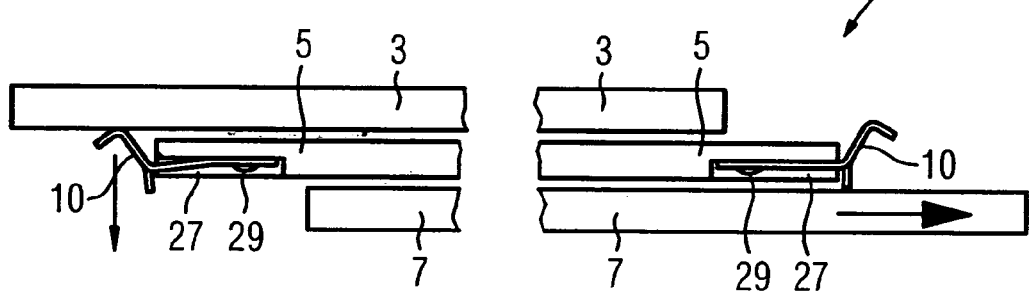
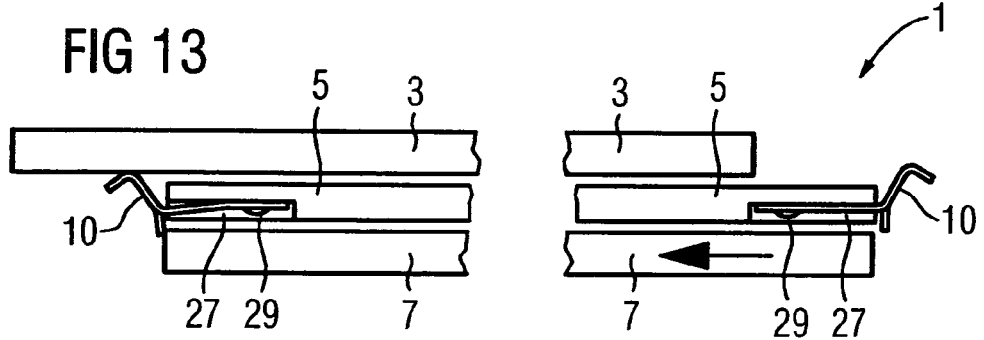
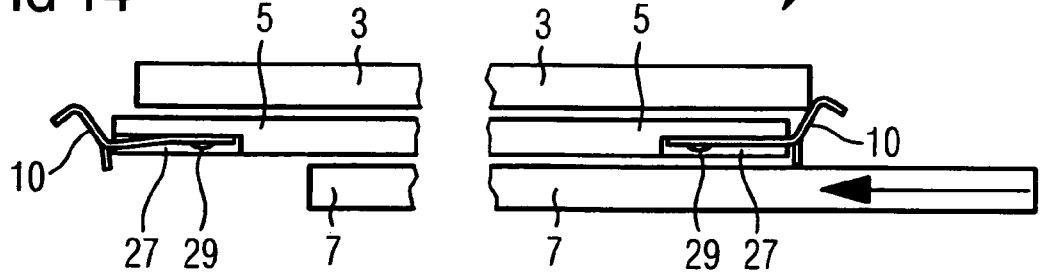

DRAWER FOR X-RAY DETECTORS

REFERENCE TO RELATED APPLICATIONS

The present patent document claims the benefit of the filing date under 35 U.S.C. §119(e) of provisional U.S. patent application Ser. No. 60/525,776, filed Nov. 28, 2003, which is hereby incorporated by reference.

BACKGROUND

The invention relates, in general, to detector drawers in X-ray systems, and more particularly, to a telescoping rail comprising a plurality of rail elements with a driver for displacement motions of the rail elements relative to one another.

Telescoping rails may be used for longitudinally displaceable support of objects. For instance, they are used in drawers, in drawer-like devices such as detector drawers in X-ray systems, or in longitudinally adjustable tripods or mounts. The ability of compressing them and pulling them apart in a telescoping fashion may enable, similarly to a telescoping antenna, obtaining a long operative length in the pulled-apart or extended state and yet requiring relatively minimal space in the compressed or retracted state. In contrast to a telescoping antenna, in telescoping rails, a separate mechanism may be provided to assure that rail elements, located between the telescoping rails comprising more than two rail elements, follow the predetermined displacement motion while being pulled apart and pushed together. These rail elements are thus configured to be operatively slaved during the displacement motions engendered by the pulled-apart and compressed states. Typically, end stops on both longitudinal ends of each rail element are provided to mark end of travels or displacements for the compressed and pulled-apart states.

End stops enable the automatic correct positioning of intermediate rail elements only in the completely pulled-apart or completely compressed states. For in-between states of the telescoping rail, the end stops may not provide for a controlled positioning of the intermediate rail elements. Certain applications require that telescoping rails be capable of being pulled out in more than a single direction. Such applications may for instance be camera tripods or X-ray detector drawers of patient examination tables. For telescoping rails that can be pulled apart on both ends, conventional end stops are problematic in the sense that intermediate rail elements can be pushed out at the opposite side upon compression from one direction, instead of stopping and remaining at predetermined positions. As such, in X-ray detector drawers of patient examination tables, this arrangement may for instance mean that after the X-ray detector has been inserted into the examination table, such intermediate rail elements, may protrude from the examination table, thus creating a hindrance and a danger.

OBJECT AND SUMMARY

The present invention is defined by the following claims. This description summarizes some aspects of the present embodiments and should not be used to limit the claims.

One object is to create an at least three-piece telescoping rail in which there between rail elements may automatically assume predetermined displacement positions in a longitudinal direction, regardless of any end stops that may be provided.

A telescoping rail has at least three rail elements movable relatively to one another. The rail elements include a basic or upper rail element, an intermediate rail element that is displaceable relative to the basic rail element, and an end or lower rail element that is displaceable relative to the intermediate rail element, in which a slaving device that includes at least one driver is disposed between the intermediate rail element and the end rail element and/or between the intermediate rail element and the basic rail element. The at least one driver is pivotably supported about a shaft oriented transversely or in inclined fashion to the displacement direction of the end rail element. The at least one driver is further configured, as a function of the intermediate rail element having been displaced out of its basic position, to be pivotable about the shaft into a slaving position, in which, as a function of a displacement of the end rail element, the intermediate rail element is displaced along with it in the direction of the basic position until the basic position is reached. In addition to end positions that might be predetermined by end stops, a basic position can be predetermined when the intermediate rail element is automatically pushed upon compression of the telescoping rail. Thus, in addition to the end stop positions, a further position, called the basic position, for the intermediate rail element is provided.

An advantageous feature is that the driver, as a function of a displacement of the intermediate rail element, may be pivoted past the basic position around the shaft out of the slaving or supportive position into a fundamental or intermediate position, in which position the intermediate rail element is not displaced. This arrangement has the advantage that the driver, upon reaching the basic position, is automatically deactivated, as it no longer slaves the intermediate rail element that is in the basic position. Because of the deactivation of the driver in the basic position, a directionally independent operative basic position for the intermediate rail element may be predetermined, notably for telescoping rails that can be pulled apart from both sides.

In a further advantageous feature, the driver is configured, when in the fundamental position, to enter into engagement with the basic rail element so as to substantially firmly hold the intermediate rail element in the basic position. In the basic position of the rail elements, the driver may bring about an active fixation in the basic position, so that uncontrollable frictional resistances, for instance, may not cause an unintended displacement of the intermediate rail element upon displacement of the end rail element.

In a further advantageous feature, the driver is configured as a pivoting part supported in a shaft. As such, a mechanism that runs smoothly, depending on the configuration of the shaft bearing, for the motion of the driver is provided and may be relatively easily realized.

In an alternately advantageous feature, the driver is configured as an elastic molded part. As such, a mechanism that may benefit from a further relatively easy realization is provided, but upon whose actuation the elastic forces of the molded part must be overcome, which may otherwise impair a smoothness or ease of displacement.

In an advantageous use, the telescoping rail is used in a patient examination table. Patient examination tables that are used for X-ray systems have a detector drawer for receiving an X-ray detector. The X-ray detector is disposed below the top of the examination table and parallel to it and can be pulled out of the patient examination table from the side. A guidance of the X-ray detector drawer can be realized via the above described telescoping rails. In a further advantageous feature, the detector drawer may be designed or configured to be pulled out from both sides of the patient examination table. In such detector drawers, as a basic position for the intermediate rail elements, a position that is located inside the table can be predetermined by the slaving device, so that intermediate rail elements may not be pushed unintentionally all the way out of the table.

Illustrative and exemplary embodiments of the invention are described in further detail below with reference to and in conjunction with the figures.

BRIEF DESCRIPTION OF THE DRAWINGS

FIG. 11 illustrates schematically another embodiment of a three-part telescoping rail in the basic position with a slaving device, in a side view;

FIG. 12 illustrates schematically the telescoping rail of FIG. 11 while being pulled apart, in a side view;

FIG. 13 illustrates schematically the telescoping rail of FIG. 12 while being compressed, in a side view;

FIG. 14 illustrates schematically the telescoping rail of FIG. 12 while being compressed, in an alternate position in a side view;

DETAILED DESCRIPTION OF THE DRAWINGS

Figure 1:
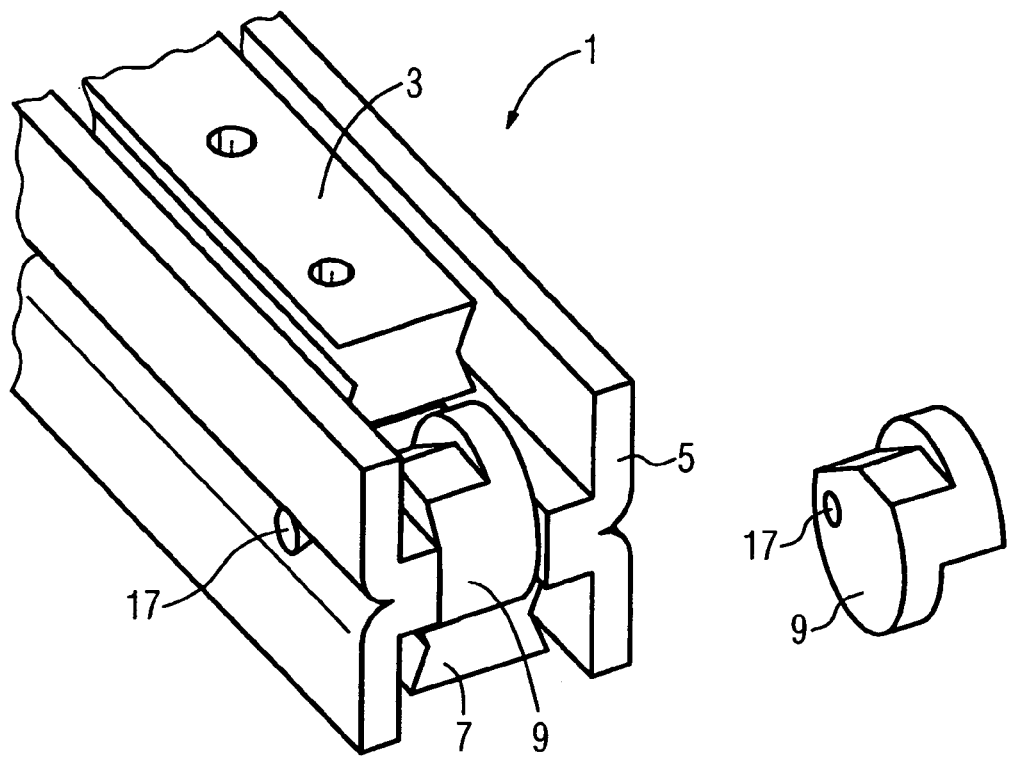
FIG. 1 illustrates schematically one embodiment of a three-part telescoping rail with a slaving device, in a perspective view.

In FIG. 1, a telescoping rail 1 is shown in a perspective view. The telescoping rail includes a basic or upper rail element 3, a double-T-shaped intermediate rail element 5, and a lower or end rail element 7. The rail elements are supported longitudinally displaceably one inside the other, but various displacement facilitating slide bearings are not shown in FIG. 1. At the end of the intermediate rail element 5, a pivoting part 9 is pivotably supported, as a driver, on a shaft 17 and is a component of the slaving device.

In the separate FIG. 1 drawing of the pivoting part 9, the shaft bearing for the shaft 17 is disposed eccentrically in the pivoting part 9, which in outline is rotationally symmetrical. The eccentric arrangement enables the automatic pivoting of the pivoting part 9 upon displacement of the rail elements. As shown, the pivoting part 9 is configured as graduated or flattened halfway on each side, but may also be disk-shaped.

Figure 2:
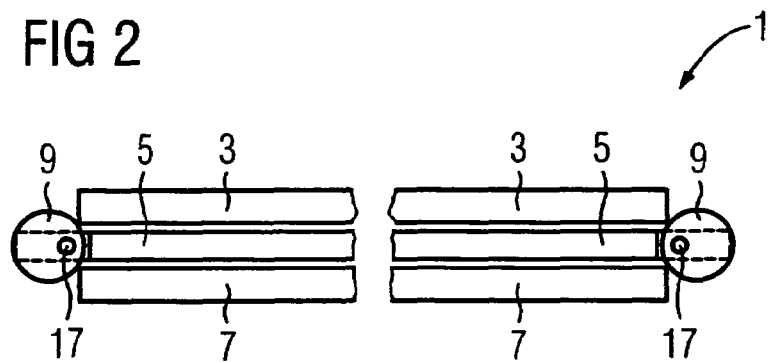
FIG. 2 illustrates schematically the telescoping rail of FIG. 1 in the basic position, with the slaving device, in a side view.

In FIGS. 2 through 5, the telescoping rail 1 of FIG. 1 is shown schematically in a side view, using the same reference numerals. FIG. 2 shows the telescoping rail in the compressed state, in a basic position. One pivoting part 9 of the slaving device is pivotably supported in a shaft 17 on each end of the intermediate rail element 5.

Figure 3:
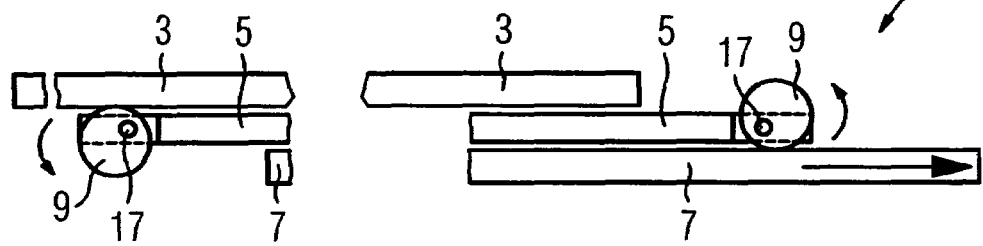
FIG. 3 illustrates schematically the telescoping rail of FIG. 1 while being pulled apart, in a side view.
Figure 4:
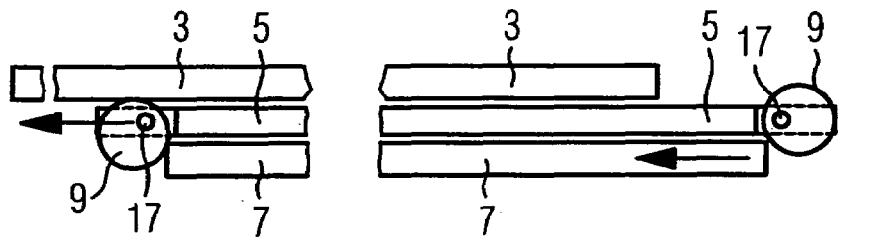
FIG. 4 illustrates schematically the telescoping rail of FIG. 1 while being compressed, in a side view.

In FIG. 3, the pivoting parts 9 are pivoted when the telescoping rail is pulled apart. The motion or displacement of the rail elements is indicated by respective arrows. The pivoting part 9 shown on the left in the drawing is pivoted into a different position, namely downward in the drawing, when the intermediate rail element 5 is pulled out by the basic or upper rail element 3. For example, the pivoting part 9 may be pivoted simply by the force of gravity. As shown in FIG. 4, this is the slaving or supporting position of the pivoting part 9. The pivoting part 9 shown on the right in the drawing is conversely pivoted in the opposite direction, namely upward in FIG. 3 and hence into a fundamental position. The pivoting parts 9 have no slaving or responsive function while the telescoping rail 1 is being pulled apart.

In FIG. 4, upon compression of the telescoping rail 1, the lower or end rail element 7 is thrust against the pivoting part 9 on the left-hand side. Since in this drawing the pivoting part 9 is in a slaving or supportive position, the intermediate rail element 5, in which the pivoting part 9 is supported, is slaved by or responsive to the motion of the end rail element 7. The intermediate rail element 5 is as such automatically jointly displaced or slaved in the direction of the compressed basic position of the telescoping rail 1. The pivoting part 9 shown on the right of FIG. 4 is in its fundamental or intermediate position and has no slaving action here.

Figure 5:
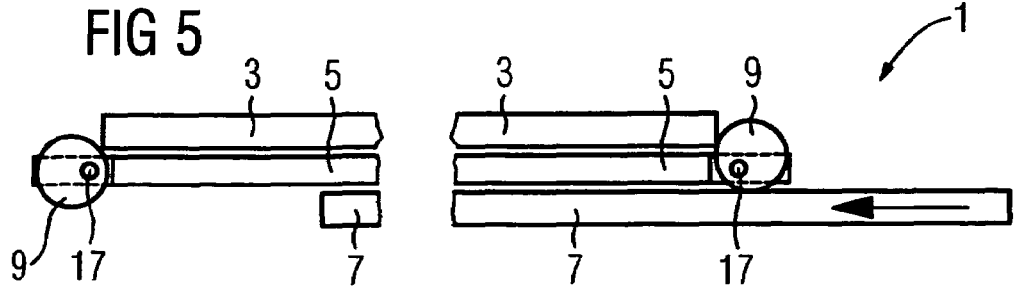
FIG. 5 illustrates schematically the telescoping rail of FIG. 1 while being compressed, at an alternate position in a side view.

In FIG. 5, an alternate position of the telescoping rail 1 upon compression is shown. The intermediate rail element 5 is already in the basic position. The pivoting part 9 shown on the left, in the position shown, is in the fundamental position and has no slaving action; the pivoting part 9 shown on the right is likewise in the fundamental position and is present at the edge of the basic rail element 3. The fundamental position of the pivoting part 9 on the right therefore assures that upon displacement of the end rail element 7 into the basic position, or in other words upon compression of the telescoping rail 1, the intermediate rail element 5 is not slaved and may be displaced out of its basic position. The pivoting part 9 enters into mutual engagement with the basic rail element 3 so as to substantially firmly hold the intermediate rail element 5 in the basic position while restricting it from sliding through.

Accordingly, the fundamental position of the pivoting parts 9 is defined such that the intermediate rail element 5 is kept in the basic position, while the slaving position is defined such that the intermediate rail element 5 is slaved with the end rail element 7 and accordingly displaced with the end rail element 7.

Because of the symmetrical construction of the telescoping rail 1 described in the preceding drawings, the telescoping rail 1 may be pulled apart in both directions, and that via the pivoting parts 9, a slaving device or mechanism is formed which upon compression assures the joint displacement of the intermediate rail element 5 into the basic position and being firmly held there upon further displacement of the end rail element 7.

Figure 6:
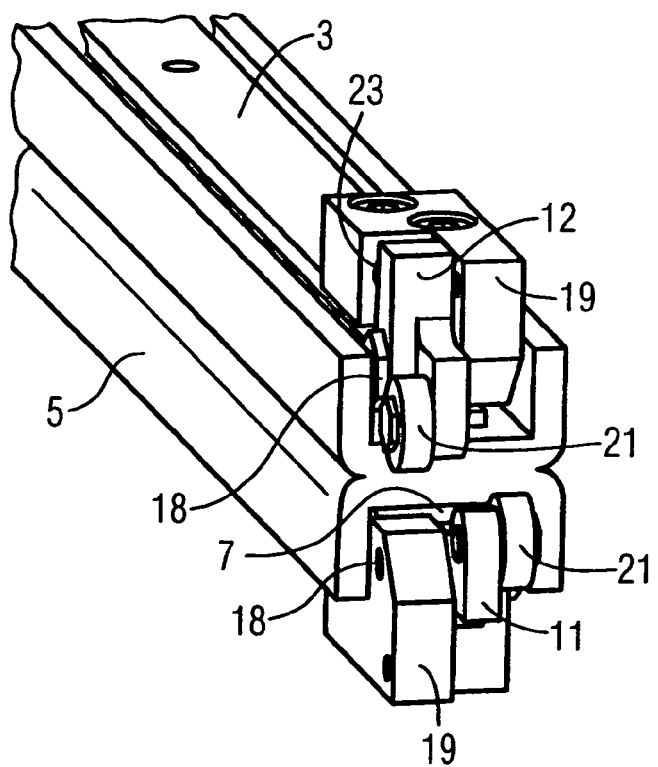
FIG. 6 illustrates schematically an embodiment of a three-part telescoping rail with a slaving device, in a perspective view.

In FIG. 6, a three-part telescoping rail 1 with a basic or upper rail element 3, an intermediate rail element 5 and an end or lower rail element 7 is shown as an alternate slaving device. For a driver, the slaving device includes a pivoting part 12 affixed at an end of the basic rail element 3 and a pivoting part 11 as a driver on the end rail element 7; one roller 21 each is rotatably supported on these pivoting parts 11, 12. The pivoting parts 11, 12 are each supported pivotably about a shaft 18 in the respective spring bearing 19. Also supported in each spring bearing 19 is a respective spring 23, which acts upon the respective pivoting part 11, 12 with a pressure force, so as to force the respective pivoting part 11, 12 around the respective shaft 18 away from the spring bearing 19.

Figure 7:
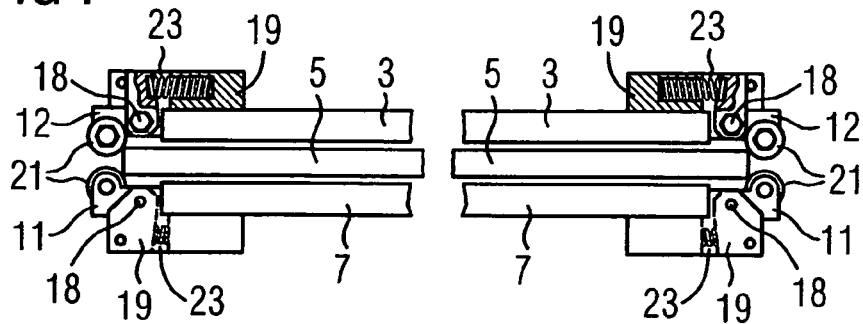
FIG. 7 illustrates schematically the telescoping rail of FIG. 6 in the basic position, in a side view.

In FIGS. 7 through 10, the telescoping rail 1 of the preceding FIG. 6 is shown schematically in a side view, using the same reference numerals. FIG. 7 shows the telescoping rail 1 in the compressed state. The intermediate rail element 5 and the end rail element 7 are accordingly in their respective basic positions. On both ends of both the basic rail element 3 and the end rail element 7, a respective pivotably supported pivoting part 11, 12 is affixed. In the respective spring supports 19, the pivoting parts 11, 12 are supported pivotably in shafts 18 that are oriented parallel to one another. The pivoting parts 11, 12 are acted upon by the respective springs 23 with a pressure force, so that the respective rollers 21 are each pressed in the direction of the intermediate rail elements 5. As such, the rollers 21 are pressed into the respective slaving position. The slaving position of the pivoting parts 12 disposed on the basic rail element 3, however, has a different function from those disposed on the end rail element 7, as will become apparent from the ensuing drawing description.

Figure 8:
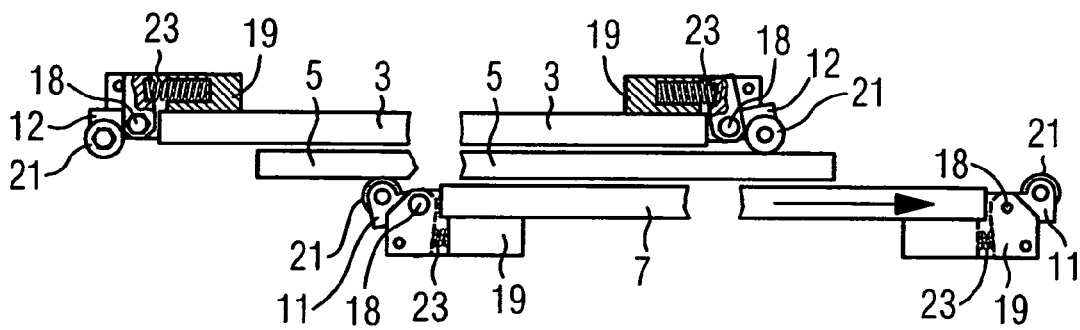
FIG. 8 illustrates schematically the telescoping rail of FIG. 6 while being pulled apart, in a side view.

In FIG. 8, the telescoping rail 1 is shown while being pulled apart. The motion of the rail elements, as above, is indicated by respective arrows. Both the pivoting part 12 shown at top right and the pivoting part 11 shown at bottom left are pressed into their respective fundamental position, in the state shown, by the intermediate rail element 5 counter to the force of the respective spring 23. In the position shown, the pivoting parts 11, 12 have no slaving action.

Figure 9:
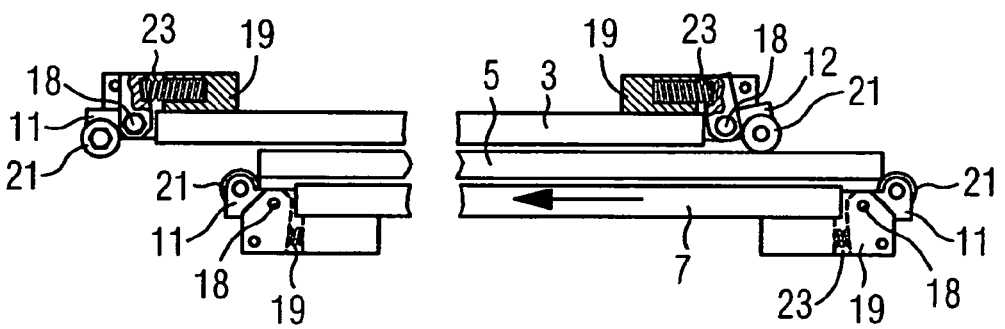
FIG. 9 illustrates schematically the telescoping rail of FIG. 6 while being compressed, in a side view.

In FIG. 9, the telescoping rail 1 is shown upon compression. The intermediate rail element 5 is engaged and slaved by the pivoting part 11 shown at the bottom right, which is in the slaving position, or by the respective roller 21. As such, upon compression, the intermediate rail element 5 is jointly displaced into the basic position by the end rail element 7. In the position shown, the other pivoting parts 11, 12 have no slaving function.

Figure 10:
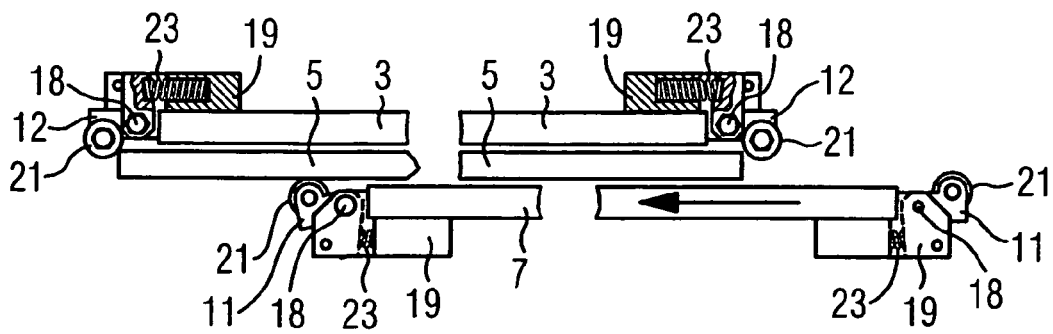
FIG. 10 illustrates schematically the telescoping rail of FIG. 6 while it is being compressed, in an alternate position in a side view.

In FIG. 10, the telescoping rail 1 is shown upon compression in a different position. The intermediate rail element 5 is already in its basic position. The intermediate rail element 5 is kept in this basic position by the pivoting part 12 shown at top left, which is in the slaving position, and corresponding roller 21 restricting it from being pushed through due to the contact with the left edge. The other pivoting parts 11, 12 have no slaving function in the position shown, so that the intermediate rail element 5, despite the displacement motion of the end rail element 7, is not displaced but rather remains in the basic position.

From the symmetrical construction of the telescoping rail 1 shown in the above FIGS. 7 through 10, this telescoping rail 1 enables being pulled apart in both directions, and in the process, upon compression, the intermediate rail element 5 is thrust into and not beyond the basic position in either direction.

From the description of FIG. 10, the pivoting parts 12 disposed on the basic rail element 3 can likewise assume both a fundamental position and a slaving position, but their slaving position serves to substantially firmly hold the intermediate rail element 5 in the basic position; that is, the intermediate rail element 5 is not slaved by the motion of the end rail element 7. Although, in this arrangement the pivoting parts 12 cannot develop any slaving action, the term "pivoting position" for the slaving position has been chosen to conform to the terms for the pivoting positions of the pivoting parts 11. Thus, the pivoting parts 12 disposed on the basic rail element 3 would, in their slaving position, have a slaving action whenever the basic rail element 3 is displaced relative to the other rail elements, i.e. whenever the displacement is viewed simply from the direction of the basic rail element 3.

In FIG. 11, an alternate three-part telescoping rail 1 with a slaving device is shown. The drawing shows a side view of the telescoping rail 1 with a basic rail element 3, an intermediate rail element 5, and an end rail element 7. As a driver, one elastic molded part 10 each is supported in both ends of the intermediate rail element 5. The molded part 10 may be secured by a respective spot weld 29 in the intermediate rail element 5 and may be supported in an open molded part bearing 27 so as to be pivotable by sagging downward in the direction of the shorter arm. Alternatively to a welded connection, the molded part may be riveted or screwed. The elastic sagging of the respective molded part 10 may act as a pivoting motion of the two arms of the respective molded part 10 into the respective slaving position.

In the schematic views in FIGS. 12 through 14, the mode of operation of the slaving device shown in the preceding FIG. 11 is shown. In FIG. 12, the telescoping rail 1 is shown on being taken or pulled apart. As above, the motion of the rail elements is represented by respective arrows. The molded part 10 shown on the right in the drawing is in the fundamental position, while the molded part 10 shown on the left has pivoted into the slaving position. In the state shown, neither of the molded parts have any slaving action.

In FIG. 13, the telescoping rail 1 is shown upon compression. The molded part 10 shown on the right in the drawing is in the position of repose and has no slaving function whatever. Conversely, the molded part 10 shown on the left is in the slaving position, and the left edge of the end rail element 7 is in contact with the shorter arm of the molded part 10. When the end rail element 7 is pushed inward, the intermediate rail element 5 is therefore slaved by the molded part 10 on the left and jointly displaced in the direction of the basic position.

In FIG. 14, the telescoping rail 1 is also shown upon compression. However, the intermediate rail element 5 here is already in the basic position, and therefore both molded parts 10 have pivoted into the fundamental position and have no slaving function. When the end rail element 7 is pushed inward, the intermediate rail element 5 is therefore not slaved. In addition, the molded part 10 shown on the right in the drawing is in contact with its longer arm, at the top with the right-hand edge of the basic rail element 3, and therefore blocks the motion of the intermediate rail element 5. As such, the intermediate rail element 5 is substantially firmly held in the basic position, and is restricted from being pushed all the way through.

Because of the symmetrical construction of the telescoping rail 1 described in the above drawings, the telescoping rail 1 can be pulled apart in both directions, and that the molded parts 10 form a slaving device which upon compression from both directions assures the displacement of the intermediate rail element 5 into the basic position and restricts it from being pushed through beyond that.

Figure 15:
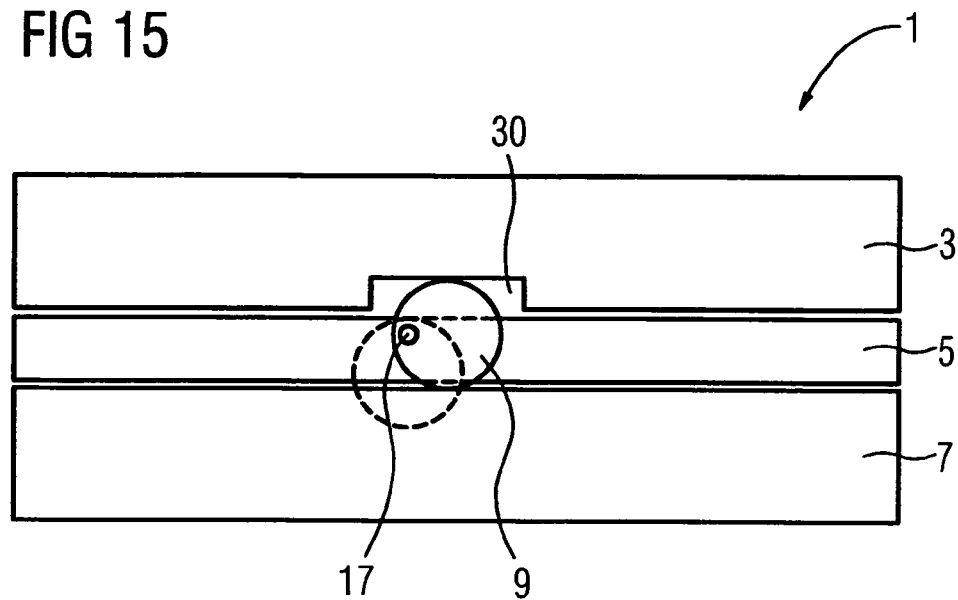
FIG. 15 illustrates schematically yet another embodiment of a three-part telescoping rail with a slaving device disposed centrally, in a side view.

In FIG. 15, a simplified embodiment of the telescoping rail 1 with a slaving device is shown schematically. The telescoping rail 1 includes a basic rail element 3, an intermediate rail element 5, and an end rail element 7. As a driver, a pivoting part 9 is pivotably supported in a shaft 17 in the intermediate rail element 5. The basic rail element 5 has a recess 30 where the pivoting part 9 assumes the fundamental position. In the position shown, the pivoting part 9 is pivoted into the recess

30. The pivoting part 9 is accordingly in the fundamental position and is not slaved upon displacement of the end rail element 7. At the same time, the motion of the pivoting part 9 in both directions of displacement is limited by the edges of the recess 30, so as to substantially firmly keep the intermediate rail element 5 in the basic position. When the telescoping rail 1 is pulled apart, the pivoting part 9, once no longer blocked by the end rail element 7, is pivoted out of the position of repose into the slaving position shown in dashed lines. As such, on the one hand, upon pulling apart of the telescoping rail the intermediate rail element 5 can be pushed out of the basic position; on the other hand, the intermediate rail element 5 that has been pushed out can upon compression be slaved by the pivoting part 9 with the end rail element 7 in the manner explained above.

Figure 16:
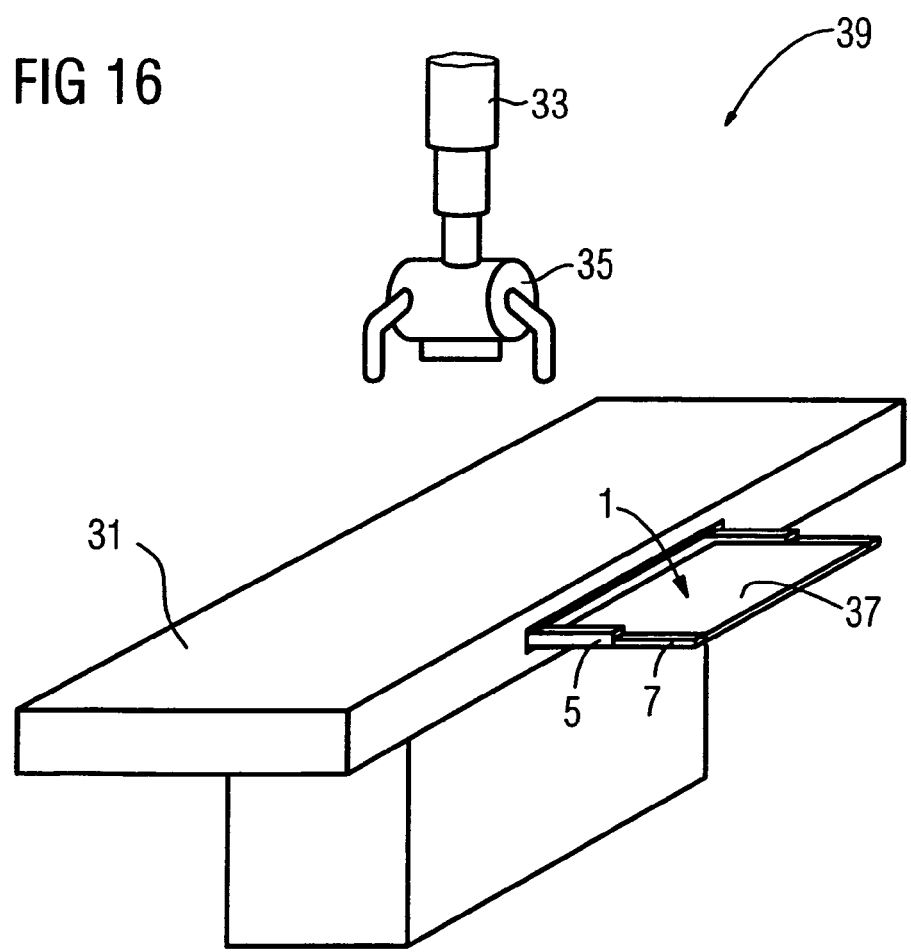
FIG. 16 illustrates schematically one embodiment of an X-ray system and a telescoping rail in the patient examination table.

In FIG. 16, an X-ray system 39 with an X-ray emitter 35 and a patient examination table 31 is shown in a perspective view. The X-ray emitter 35 is secured to a ceiling mount 33, which can be displaced vertically in telescoping fashion. A displacement of the ceiling mount 33 in the horizontal direction may also be provided.

The patient examination table 31 has a receptacle into which an X-ray detector 37 can be inserted. The X-ray detector is guided via a multi-part telescoping rail 1, which enables the X-ray detector 37 to be pushed into and pulled out of the patient examination table 31. The telescoping rail 1 is in at least three parts and has one of the slaving devices described above, although not shown in detail in the drawing. Furthermore, the receptacle is designed such that the X-ray detector 37 can be pulled out on both opposite sides of the patient examination table 31, likewise not shown in detail in this drawing. The slaving device of the telescoping rail 1 is configured to define a basic position in which all the rail elements of the telescoping rail 1 are located inside the patient examination table 31. As such, when the X-ray detector 37 is pushed in, the intermediate rail element 5, for instance, is not pushed into the table and pushed out again on the other side due to the insertion motion of the end rail element 7.

The invention claimed is:

1. A telescoping rail comprises:
   a basic rail element;
   an intermediate rail element that is displaceable relative to the basic rail element;
   an end rail element that is displaceable relative to the intermediate rail element, and
   a slaving mechanism that includes at least one disklike driver connected to the intermediate rail element,
   wherein the at least one disklike driver is pivotably supported about an axis that is free of intersection of the basic rail element and the end rail element, and
   wherein as a function of the intermediate rail element being displaced out of a basic position, the at least one disklike driver is pivotable into a slaving position which displaces the intermediate rail element in a direction of the basic position until the basic position is reached as a function of a displacement of the end rail element.

2. The telescoping rail of claim 1, wherein the at least one disklike driver, as a function of a displacement of the intermediate rail element, is pivotable past the basic position around the shaft out of the slaving position into a fundamental position, such that jointly displacing the intermediate rail element is minimized.

3. The telescoping rail of claim 2, wherein the at least one disklike driver is configured, while in the fundamental position, to enter into engagement with the basic rail element so as to firmly hold the intermediate rail element in the basic position.

4. The telescoping rail of claim 2, wherein the at least one disklike driver is configured, while in the fundamental position, to enter into engagement with the basic rail element so as to firmly hold the intermediate rail element in the basic position.

5. The telescoping rail of claim 1, wherein the at least one disklike driver is configured as a pivoting part supported in a shaft.

6. The telescoping rail of claim 1, wherein the at least one disklike driver is an elastic molded part.

7. The telescoping rail of claim 1, wherein the end rail element is displaceable relative to the basic rail element out of the basic position in both longitudinal directions.

8. In a patient examination table having a telescoping rail, an improvement in the telescoping rail comprising:
   a basic rail element;
   an intermediate rail element that is longitudinally displaceable relative to the basic rail element;
   an end rail element that is longitudinally displaceable relative to the intermediate rail element; and
   a slaving mechanism that includes at least one disklike driver connected to the intermediate rail element,
   wherein the at least one driver is pivotably supported about an axis that is free of intersection of the basic rail element and the end rail element, and
   wherein as a function of the intermediate rail element being displaced out of a basic position, the at least one disklike driver is pivotable in the shaft into a slaving position which displaces the intermediate rail element in a direction of the basic position until the basic position is reached as a function of a displacement of the end rail element.

9. The patient examination table of claim 8, wherein the at least one disklike driver, as a function of a displacement of the intermediate rail element, is pivotable past the basic position around the shaft out of the slaving position into a fundamental position, such that jointly displacing the intermediate rail element is minimized.

10. The patient examination table of claim 8, wherein the at least one disklike driver is configured, while in the fundamental position, to enter into engagement with the basic rail element so as to firmly hold the intermediate rail element in the basic position.

11. The patient examination table of claim 8, wherein the end rail element is displaceable relative to the basic rail element out of the basic position in both longitudinal directions.

12. An X-ray system having a patient examination table which includes a telescoping rail, the X-ray system comprising:
   an X-ray emitter positioned relative to the patient examination table;
   the telescoping rail comprising:
      a basic rail element;
      an intermediate rail element that is longitudinally displaceable relative to the basic rail element;
      an end rail element that is longitudinally displaceable relative to the intermediate rail element; and
      a slaving mechanism that includes at least one disklike driver connected to the intermediate rail element,
      wherein the at least one disklike driver is pivotably supported about an axis that is free of intersection of the basic rail element and the end rail element, and
      wherein as a function of the intermediate rail element being displaced out of a basic position, the at least one disklike driver is pivotable about the shaft into a slaving position which displaces the intermediate rail element in a direction of the basic position until the basic position is reached as a function of a displacement of the end rail element.

13. The X-ray system of claim 12, wherein the at least one disklike driver, as a function of a displacement of the intermediate rail element, is pivotable past the basic position around the shaft out of the slaving position into a fundamental position, such that jointly displacing the intermediate rail element is minimized.

14. The X-ray system of claim 12, wherein the at least one disklike driver is configured, while in the fundamental position, to enter into engagement with the basic rail element so as to firmly hold the intermediate rail element in the basic position.

15. The X-ray system of claim 12, wherein the end rail element is displaceable relative to the basic rail element out of the basic position in both longitudinal directions.

16. The telescoping rail of claim 1, wherein the at least one disklike driver of the slaving mechanism comprises only one disklike driver connected to the intermediate rail element.

* * * * *